(12) United States Patent
Swartz et al.

(10) Patent No.: US 9,243,283 B2
(45) Date of Patent: Jan. 26, 2016

(54) SYSTEM AND METHOD FOR AUTHENTICATION AND TAMPER DETECTION USING NUCLEIC ACID TAGGANTS

(71) Applicant: SRC, Inc., North Syracuse, NY (US)

(72) Inventors: Mary F. Swartz, Princeton, NJ (US); Garrett D. Liddil, Fayetteville, NY (US); Adam J. Lowe, Syracuse, NY (US)

(73) Assignee: SRC, Inc., North Syracuse, NY (US)

( * ) Notice: Subject to any disclaimer, the term of this patent is extended or adjusted under 35 U.S.C. 154(b) by 340 days.

(21) Appl. No.: 13/680,613

(22) Filed: Nov. 19, 2012

(65) Prior Publication Data

US 2014/0141984 A1 May 22, 2014

(51) Int. Cl.
*C12Q 1/68* (2006.01)
*G01N 37/00* (2006.01)
*C40B 30/04* (2006.01)

(52) U.S. Cl.
CPC .. *C12Q 1/68* (2013.01); *C40B 30/04* (2013.01)

(58) Field of Classification Search
CPC ........... C12Q 1/68; C40B 20/04; C40B 30/04
See application file for complete search history.

(56) References Cited

U.S. PATENT DOCUMENTS

| | | | |
|---|---|---|---|
| 5,139,812 A | 8/1992 | Lebacq | |
| 5,451,505 A | 9/1995 | Dollinger | |
| 5,643,728 A | 7/1997 | Slater et al. | |
| 7,235,289 B2 | 6/2007 | Rancien et al. | |
| 7,710,269 B2 | 5/2010 | Reep | |
| 2004/0166520 A1 | 8/2004 | Connolly | |
| 2004/0219287 A1 | 11/2004 | Regan et al. | |
| 2006/0073506 A1 | 4/2006 | Christians et al. | |
| 2006/0121181 A1* | 6/2006 | Sleat | D21H 21/46 427/7 |
| 2009/0075261 A1* | 3/2009 | Hayward et al. | 435/6 |
| 2009/0181381 A1 | 7/2009 | Oldham et al. | |
| 2011/0000560 A1 | 1/2011 | Miller et al. | |

FOREIGN PATENT DOCUMENTS

| | | | |
|---|---|---|---|
| WO | 8706383 | 10/1987 | |
| WO | 9855648 | 12/1998 | |
| WO | 0136676 A2 | 5/2001 | |
| WO | WO 2011070064 A1 * | 6/2011 | ............. E05G 1/005 |

OTHER PUBLICATIONS

Kidwell, "Packaging technology: Security and tamper evidence protection systems", http://www.curtec.info/uploads/Downloads/Packaging%20technology/Tamper_evidence_EN.pdf, as of Aug. 31, 2011, pp. 1-4.

* cited by examiner

*Primary Examiner* — Samuel Woolwine
*Assistant Examiner* — Kaijiang Zhang
(74) *Attorney, Agent, or Firm* — George R. McGuire; Blaine T. Bettinger; Bond Schoeneck & King, PLLC

(57) ABSTRACT

Methods for authenticating and/or detecting tampering of an item of interest using a nucleic acid tag. A nucleic acid tag comprising a nucleotide-support platform attached to a nucleic acid molecule is created or obtained and then sealed within or on the item of interest. The surface of the item of interest is sampled for the presence of the seeded tag after the item of interest has been moved from one location to another or has been stored for a period of time, during which tampering can occur and/or authentication may necessary. The presence of the tag can indicate that tampering has occurred, or that the item of interest is authentic.

9 Claims, 14 Drawing Sheets

SYSTEM AND METHOD FOR AUTHENTICATION AND TAMPER DETECTION USING NUCLEIC ACID TAGGANTS

BACKGROUND OF THE INVENTION

1. Field of the Invention

The present invention relates to systems and methods for using nucleic acid tags, and, more particularly, to systems and methods for using nucleic acid for authentication and for tampering detection.

2. Description of the Related Art

The physical characteristics of a nucleic acid molecule make it uniquely suitable for use as a secure information-storage unit. In addition to being odorless and invisible to the naked eye, a nucleic acid molecule can store vast amounts of information. It has been estimated that a single gram of deoxyribonucleic acid ("DNA") can store as much information as approximately one trillion compact discs ("Computing With DNA" by L. M. Adleman, *Scientific American*, August 1998, pg 34-41).

Nucleic acid molecules are also resilient to decay, even in vitro. Although a nucleic acid molecule typically begins to breakdown when exposed to chemicals, radiation, or enzymes, some nucleic acid molecules can survive for thousands of years. For example, scientists have sequenced the Neanderthal genome using DNA molecules that were recovered from remains dating at least 38,000 years old.

Additionally, nucleic acid molecules are both ubiquitous in nature and largely uncharacterized, with only a fraction of the world's organisms having been sequenced. As a result of this uncharacterized environmental background noise, inadvertent detection of a man-made nucleic acid molecule is unlikely.

To employ the many beneficial characteristics of nucleic acids, these molecules can be incorporated into a secure tag. These tags can be composed of deoxyribonucleotides, ribonucleotides, or similar molecules composed of nucleic acids that are either artificial (such as nucleotide analogues) or are otherwise found in nature. The nucleic acids can range from very short oligonucleotides to complete genomes.

Once a nucleic acid tag is created it can be used for numerous unique security applications including to detect illicit tampering with physical objects. DNA tags have previously been used for other applications. For example, DNA tags have been removably attached to tangible assets to assist in the identification of ownership in the event the asset is lost or stolen. Additionally, it has been proposed that DNA tags be used to prevent counterfeiting by incorporating tags into items during or after production and using detection of such tags to authenticate the items. However, there is a continued demand for new and efficient mechanisms for using nucleic acid tags to detect tampering.

BRIEF SUMMARY OF THE INVENTION

Methods and systems for authentication and tampering detection. In one aspect, a method for detecting tampering comprises the steps of: sealing within an item of interest a nucleic acid tag comprised of a nucleotide-support platform attached to a nucleic acid molecule; and examining an exterior surface of the item of interest for the presence of the nucleic acid tag, wherein the presence of the tag on the exterior surface indicates tampering.

In one implementation, the step of sealing the nucleic acid tag within the item of interest comprises releasing the nucleic acid tag inside the item of interest after the item of interest has been sealed.

In one implementation, further comprising the step of, if tampering has been detected, examining a surface other than the surface of the item of interest for the presence of the nucleic acid tag.

In one implementation, the nucleic acid molecule is composed of nucleotides selected from the group consisting of ribonucleotides, deoxyribonucleotides, and nucleotide analogues.

In one implementation, the nucleic acid molecule is an oligonucleotide.

In one implementation, information about the item of interest is contained within the nucleic acid molecule.

In one implementation, the nucleotide-support platform is a nanoparticle. In another implementation, the nucleotide-support platform is a diatom or other naturally-occurring particle.

In one implementation, the nucleic acid tag includes an encapsulant.

In one implementation, the step of sealing the nucleic acid tag within an item of interest comprises incorporating the nucleic acid tag within a label or a package of the item of interest.

In one implementation, the step of sealing the nucleic acid tag within an item of interest comprises incorporating the nucleic acid tag into a precursor of the item of interest.

In a second aspect, a method for detecting tampering with an item of interest comprises: obtaining a nucleic acid tag, wherein the nucleic acid tag comprises a nanoparticle nucleotide-support platform attached to a nucleic acid molecule, and wherein information about the item of interest is contained within the nucleic acid molecule; sealing the nucleic acid tag within the item of interest, wherein the nucleic acid tag is released inside the item of interest after the item of interest has been sealed; and examining an exterior surface of the item of interest for the presence of the nucleic acid tag, wherein the presence of the tag on the exterior surface indicates tampering.

In yet another aspect, methods and systems for authenticating an item of interest comprise the steps of adding to the item of interest a nucleic acid tag comprised of a nucleotide-support platform attached to a first nucleic acid molecule, wherein information about the item of interest is contained within the first nucleic acid molecule; sampling a portion of an item for the presence of the nucleic acid tag, wherein the item is potentially the item of interest; detecting the presence of the nucleic acid tag in the sample, wherein the presence of the first nucleic acid tag authenticates the item as the item of interest.

In one implementation, the step of adding the nucleic acid tag to the item of interest comprises the step of incorporating the nucleic acid tag into a label or a package of the item of interest.

In one implementation, the step of adding the nucleic acid tag to the item of interest comprises the step of incorporating the nucleic acid tag into a precursor of the item of interest.

In one implementation, the nucleic acid tag comprises information about the origin, manufacturing, or expiration of the item of interest.

In one implementation, a method for detecting the presence of the nucleic acid tag in the sample comprises the steps of: providing a third nucleic acid molecule, wherein at least a portion of the third nucleic acid molecule is hybridized to at least a portion of the second nucleic acid molecule; combining the sample, potentially containing the first nucleic acid molecule, with the hybridized second and third nucleic acid molecules to form a mixture; maintaining the mixture under conditions suitable for hybridization at least a portion of the first nucleic acid molecule to at least a portion of the second nucleic acid molecule, wherein when the first and second nucleic acid molecules hybridize, the third nucleic acid molecule is displaced; and detecting the displaced third nucleic acid molecule, wherein the presence of displaced third nucleic acid molecule indicates the presence of the first nucleic acid tag in the sample.

In one implementation, the second nucleic acid molecule comprises a fluorophore quencher and the third nucleic acid molecule comprises a fluorophore, and if the third nucleic acid is displaced by hybridization of the first nucleic acid molecule and the second nucleic molecule, the fluorophore is no longer quenched by the fluorophore quencher.

In one implementation, the method further comprises the step of determining the fluorescence of the mixture.

In one implementation, the fluorescence of the mixture is determined by a handheld wireless device.

In one implementation, the handheld wireless device is a smartphone.

In another implementation, the step of detecting the presence of the nucleic acid tag in the sample comprises an electrochemical detection system, including but not limited to luminescence, surface plasmon resonance, cyclic voltammetry, electrochemical impedance spectroscopy, or quartz crystal microbalance. The step of detecting the presence of the nucleic acid tag in the sample may also comprise atomic force microscopy.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
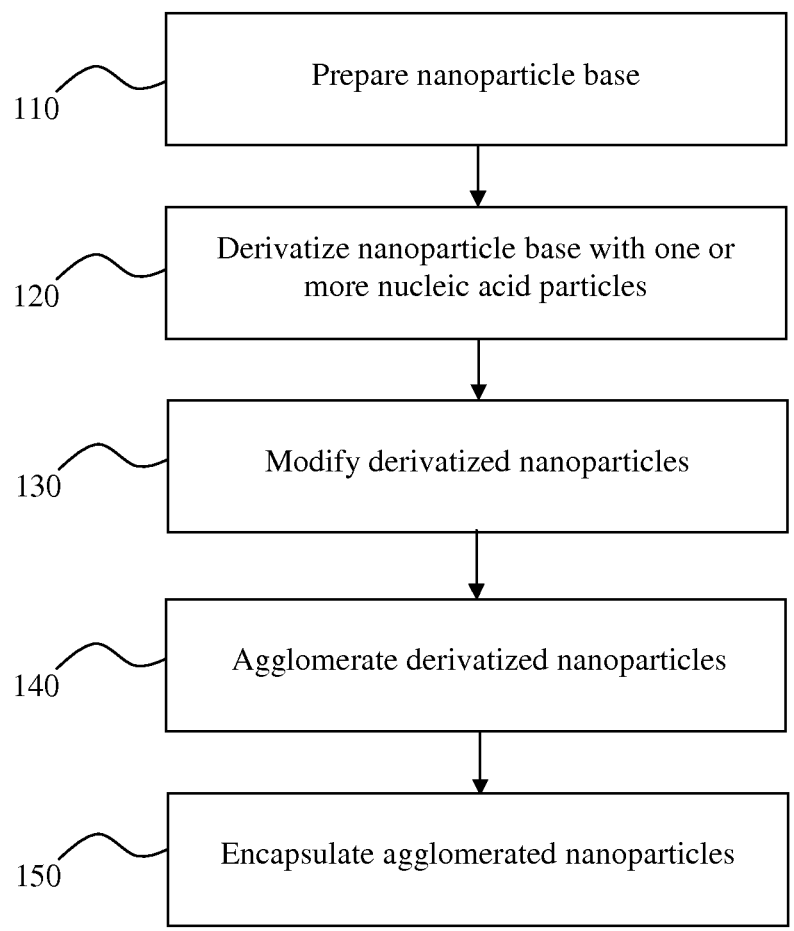
FIG. 1 is a flowchart of an exemplary process for creating a nucleic acid tag in accordance with an embodiment.

Referring now to the drawings wherein like reference numerals designate identical or corresponding parts throughout the several views, there is shown in FIG. 1 a flowchart of an exemplary process for creating a suitable nucleic acid tag in accordance with an embodiment of the present invention. As an initial step 110, a nanometer-sized particle ("nanoparticle") platform is prepared for attachment to the nucleic acid molecule(s). A platform is used to make the nucleic acid more accessible to downstream analysis and prevent nucleic acid loss if any portion of the encapsulating layer is compromised.

The platform is any compound that can be attached to nucleic acid without unintentionally degrading or altering the nucleic acid sequence. For example, the platform can be a lightweight, durable, non-water soluble, and chemically inert structure composed of silica or polystyrene. Additionally, the nanoparticle platform should be composed of a compound that does not inhibit any downstream analysis of the nucleic acid molecules, including tag detection and polymerase chain reaction ("PCR").

At step 120, the nucleic acid molecule is attached to the prepared nanoparticle platform. The nucleic acid can be any natural or artificial nucleic acid, including but not limited to deoxyribonucleotides, ribonucleotides, oligonucleotides, nucleic acid analogs, and similar molecules that are either artificial or are otherwise found in nature, as well as combinations of any or all of the above. The nucleic acids can range from a very short sequence to a complete genome, for example. The nucleic acid molecules are optimally attached to the nanoparticle to facilitate later analysis. In a preferred embodiment, a chemical linker is used to connect the nucleic acid to the nanoparticle platform. This chemical linker must keep the nucleic acid securely tethered to the nanoparticle while avoiding inhibition of the detection or analysis of the tag and nucleic acid. Although the chemical linker can be chosen to provide a permanent covalent link between the nucleic acid and the nanoparticle platform, it could also be a compound that quickly and efficiently releases the nucleic acid at a certain temperature or after exposure to a release compound.

The nucleic acid molecule can also be designed to promote analysis. For example, to avoid steric hindrance or unwanted intermolecular interactions, the molecule can include nucleotide spacers between the chemical linker or nanoparticle base and the information-coding segment of the nucleotide sequence. Spacing between 1 and 100 bases has been optimal for current applications, although this may vary as new applications are considered.

The concentration of nucleic acid molecules on the nanoparticle platform is also an important factor in downstream analysis. If the molecules are too concentrated, steric hindrance prevents the primer and polymerase from efficiently binding the proper segments of the nucleic acid molecules. If the molecules are too sparse, the PCR signal will be diminished and can result in false negatives. In a preferred embodiment, a concentration of about $1\times10^8$ to $1\times10^{12}$ nucleic acid molecules per square centimeter is the optimal concentration for robust PCR signal.

At step 130, which can occur at the position shown in the flowchart or before or after any other step after derivatization of the nanoparticles, the derivatized nanoparticles can optionally be modified for any purpose, use, or design. For example, a flame or fire retardant can be added to the derivatized nanoparticles. The flame or fire retardant is preferably anything known by those skilled in the art to inhibit combustion or reduce the temperature of associated material in response to high temperatures, including but not limited to Nomex®, GORE-TEX®, Kevlar®, aluminum hydroxide, magnesium hydroxide, hydromagnesite, calcium silicate, or halocarbons, among many others. While some compounds provide the tag with resistance to combustion, others provide the tag with thermal protection by absorbing heat in an endothermic reaction, through chemical degradation, or by otherwise protecting the tag from high temperatures.

The derivatized nanoparticles can also be modified to include an odorant. The odorant can be anything known to be capable of detection by mechanical means or by human or animal means (i.e., olfaction detection). The odorant can comprise anything known by those skilled in the art to be capable of detection, including a single aromatic, a blend of aromatics, or a commercially available synthetic chemical, among many others. Since the surfaces on which the odorant might be detected will vary, the odorant will preferably be unique or distinctive enough to be detected over random odorants present on these surfaces or in the surrounding environment. Although according to one embodiment the odorant is capable of detection by humans and/or animals, in the preferred embodiment the odorant can only be detected by animals and/or electronic means, thereby evading human detection. For example, mechanical means such as an "electronic nose" could be programmed or trained to recognize the odorant and alert the user to its presence. In a preferred embodiment, the sensor provides quantitative information about detection and is sensitive enough to detect very minute or trace amounts of the odorant.

Lastly, the tag can also be modified with other compounds to provide additional desired characteristics including but not limited to color, luminescence, or protection against ultraviolet radiation.

At step 140 of the exemplary method, the nucleic acid-derivatized nanoparticles are agglomerated. Agglomeration protects the nucleic acid molecules from degradation and facilitates encapsulation. To agglomerate the particles to the desired size range, the nanoparticles are vacuum dried, milled, and sieved.

Compounds might be used or incorporated into the tag to promote disagglomeration of the agglomerates prior to PCR analysis. These compounds might be bovine serum albumin, salmon sperm DNA, carbohydrates, polyvinyl alcohol, fructose, or chitosan, among others. With more nucleic acid exposed during dissolution, subsequent analysis will be faster and more sensitive.

After the nanoparticles are agglomerated, the agglomerates are encapsulated at step 150. The encapsulant protects the nucleic acid from degradation by ultraviolet light, hydrolysis, enzymatic digestions, chemical degradation, or any other means. Additionally, the encapsulant can be designed such that it does not hinder analysis of the nucleic acid molecules. For example, the encapsulant should not contain any compounds that would inhibit or prevent a PCR reaction, although efficient removal of the encapsulant before PCR analysis would eliminate this requirement. Additionally, the encapsulant should enhance the ability of the tag to discretely attach to people and objects. If covertness is required, the encapsulant can be designed to deter detection.

The encapsulating layer can also be designed with surface moieties added to the inner or outer surfaces of the encapsulant or incorporated into the encapsulant material. The moieties are designed to facilitate a particular use of the nucleic acid tag. For example, the moiety can be hydrophobic to enable stickiness or contain antibodies designed for specific targeting. The molecular interactions between the moiety and a target compound can range from simple electrostatic interactions to antibody-antigen recognition. The moiety can also promote detection of the nucleic acid tag.

To protect the nucleic acid from degradation, the encapsulating layer can be coated with or include another functional layer of material. For example, the encapsulant can be coated with or include a non-water-soluble compound to prevent access to water or similar molecules. The encapsulant can also be coated with or include a UV-blocking compound such as titanium dioxide to prevent UV-induced degradation of the nucleic acid molecules.

In yet another embodiment, the nucleic acid tag comprises just nucleic acid, or nucleic acid in combination with a structure or base other than a nanoparticle. For example, the nucleic acid may be unencumbered, or it may be tethered (covalently or non-covalently) to a structure or base. There may be many copies of the nucleic acid, or just a few copies, and can range from a very short sequence to a complete genome, for example. The nucleic acid can be connected to the structure or base by a chemical linker. Although the chemical linker can be chosen to provide a permanent covalent link between the nucleic acid and the structure or base it could also be a compound that quickly and efficiently releases the nucleic acid at a certain temperature or after exposure to a release compound. The nucleic acid molecule can also include nucleotide spacers between the chemical linker or nanoparticle base and the information-coding segment of the nucleotide sequence in order to avoid steric hindrance or unwanted intermolecular interactions. Spacing between 1 and 100 bases has been optimal for current applications, although this may vary as new applications are considered.

Figure 2:
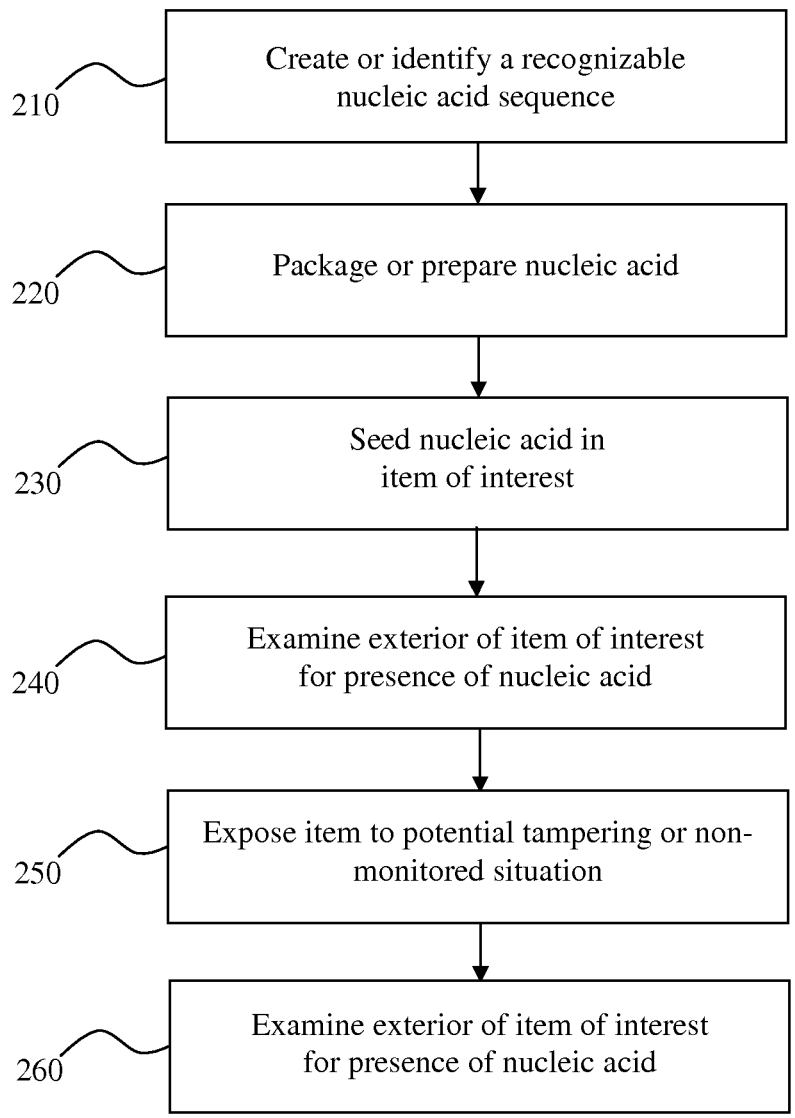
FIG. 2 is a flowchart of an exemplary process for using nucleic acid to detect tampering in accordance with an embodiment.

FIG. 2 is a schematic representation of an embodiment of a security method according to the present invention. More specifically, the figure represents a method for detecting illicit tampering with an item using nucleic acid. The item can be any person or object of interest.

As an initial step 210, a suitable nucleic acid sequence is characterized or created. In one embodiment of the present invention, the sequence ranges from a short oligonucleotide to an entire genome and is generated through any of the various known methods of natural or artificial nucleic acid synthesis. The nucleic acid can be completely composed of either natural nucleic acids which normally compose the genomes of organisms, artificial nucleic acids, or any combination thereof.

In a preferred embodiment, the nucleic acid molecules contain primer-binding sequences surrounding unique nucleotide sequences. The unique nucleotide sequence contained between the primers can encode information that corresponds to an identification, location, date, time, or other data specific to that unique sequence. Since analysis of every nucleic acid molecule can use the same primers, the analysis can be performed faster and more efficiently.

The primer sequences, whether they are unique or identical for each location or use, are chosen to avoid cross-reactions with naturally-occurring nucleic acid molecules in the environment in which the nucleic acid is located. Although only a fraction of natural nucleic acid molecules on Earth have been characterized by scientists, the search of nucleic acid repository databases such as GenBank®, the National Institutes of Health database containing all publicly available DNA sequences, could be a preliminary step in constructing the primer sequences.

In one embodiment of the current invention, unique groupings of nucleotides are assigned a specific letter, number, or symbol value in order to encode information within the sequence. By placing the unique groupings in order, information can be encrypted into the nucleotide sequence. To further increase the security of the information, advanced encryption algorithms can be used to assign letter, number, or symbol values to specific nucleotides or nucleotide groupings. Additionally, the encryption system can be periodically changed to prevent decryption by intercepting entities.

The nucleic acid can also be encoded to contain information other than a string of letters, numbers, and symbols. For instance, the sequence can be a random sequence that corresponds to the item, location, or date that the object of interest will be seeded. Alternatively, the tag can be as simple as a single nucleic acid change in a previously identified or known sequence. For example, the nucleotide sequence can be embedded in a full or partial genomic sequence corresponding to an organism which naturally exists in the location to be seeded. Modifications to the natural nucleic acid sequence, known only to the creator of the tag, can be made such that the changes resemble natural variations of the sequence and thus fail to arouse suspicion, even by individuals that might suspect such tags are present.

To decrypt the encoded information according to this system, an individual will need: (1) knowledge that encoded nucleic acid is present; (2) knowledge of the specific location of the information within the nucleic acid in order to use the appropriate primers for amplification and sequencing reactions; (3) access to a PCR machine and reagents; and (4) the encryption algorithm, or, alternatively, complex decryption capabilities.

Although creating the nucleic acid target within the genome of an naturally-occurring organism provides numerous benefits, both in vivo and in vitro DNA replication occasionally introduces random errors into a DNA sequence despite the actions of proof-reading and repair enzymes. By deleting one or more nucleotides or frame-shifting the nucleic acid sequence, these mutations can disrupt any encrypted information contained therein. Computer algorithms are used to restore the information by recognizing and repairing the errors. For example, if a mutation adds one or more nucleotides to a pre-defined sequence and disrupts the information, the algorithm removes single or multiple nucleotides from the sequence until the information is corrected. Similarly, if a mutation removes one or more nucleotides, the algorithm systematically adds nucleotides to the sequence until the information is corrected. The algorithm must also be robust enough to decrypt sequences that contain more than one type of error-inducing mutation, and must be capable of recognizing when the information contained with the nucleic acid has been restored.

In step 220 of the exemplary method shown in FIG. 2, the nucleic acid is packaged, prepared, or otherwise modified prior to use. Preparation of the nucleic acid can range from little or no preparation or modification to an extensive series of steps for modifying the nucleic acid. For example, the nucleic acid can be used to derivatize nanoparticles, as described above, or can be added to another structure or base.

Figure 3:
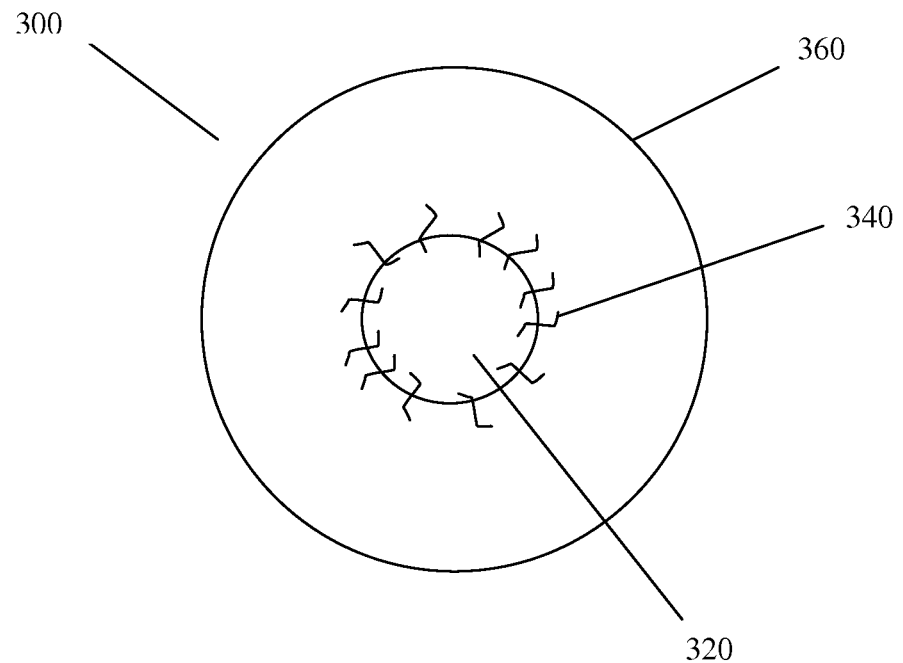
FIG. 3 is a side view of a nucleic acid tag complex in accordance with an embodiment.

As another example, the nucleic acid can be packaged into an appropriate tag complex. To avoid potentially harmful environmental side-effects, the tag can be large enough to avoid being inhaled by people or organisms but small enough to be covert. FIG. 3 represents one embodiment of this tag structure. Tag 300 is composed of a single nucleotide-support platform 320, nucleic acid 340, and encapsulant 360.

Figure 4:
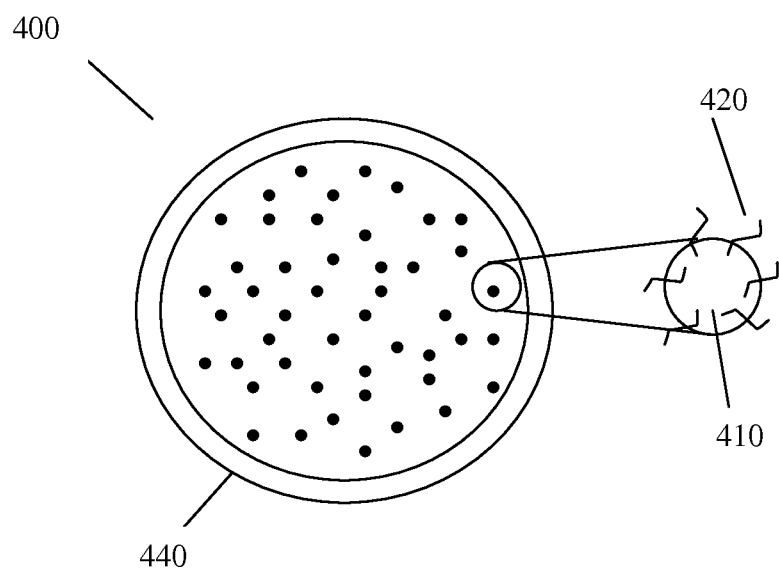
FIG. 4 is a side view of encapsulated nucleotide-derivatized nanoparticles in accordance with an embodiment.

FIG. 4 is a side view of another embodiment of a tag structure. Tag 400 is composed of nucleotide-support platform 410 derivatized with nucleic acid 420 and surrounded by encapsulant 440. Similar to the tag in FIG. 3, tag 400 contains nucleic acids that are contained within an encapsulant that protects the sequence without inhibiting later analysis. Unlike the bead platform used by the tag in FIG. 3, nucleotide-support platform 410 is composed of nanoparticles. Tag 400 can contain thousands, millions, or even billions of nucleotide-derivatized nanoparticles within the encapsulant layer.

In yet another embodiment, the tag complex can be modified to include, comprise, or be associated with an additional element 500 such as a unique identifier, a fire or flame retardant, a UV-protectant, a waterproof element, and/or an odorant, among many other types of modification. For example, a fire or flame retardant can protect the tag by resisting combustion or lowering high external temperatures. A fire- or high temperature-resistant tag can be used for many different applications, including those where the tag is expected to be exposed to fire or the high temperature of an explosion. The tags can be used to detect tampering in areas or on items or individuals suspected to be involved in the constructions of bombs or other incendiary devices, and the fire- or heat-resistant element would help the tamper tag survive the explosion, which could then be analyzed using downstream processes.

Figure 5:
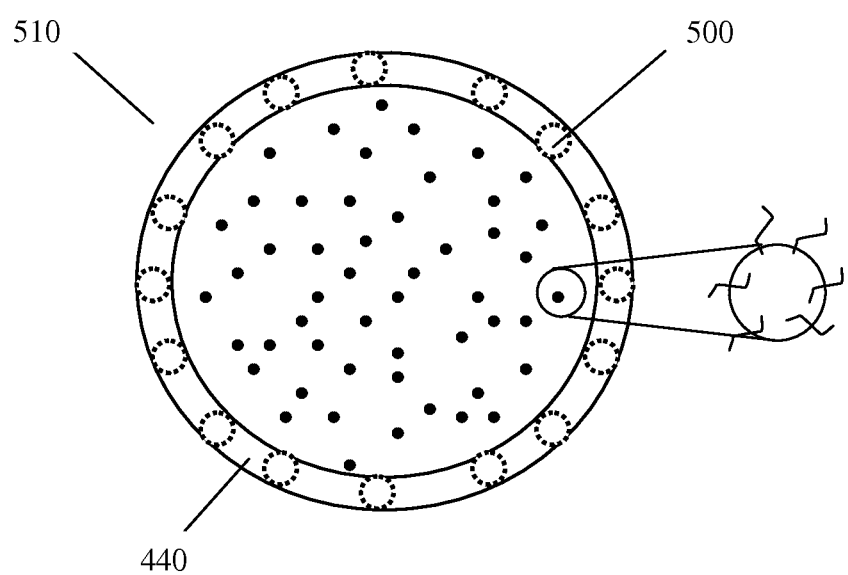
FIG. 5 is a side view of an encapsulated nucleotide tag complex with marker elements incorporated into the encapsulant layer in accordance with an embodiment.
Figure 6:
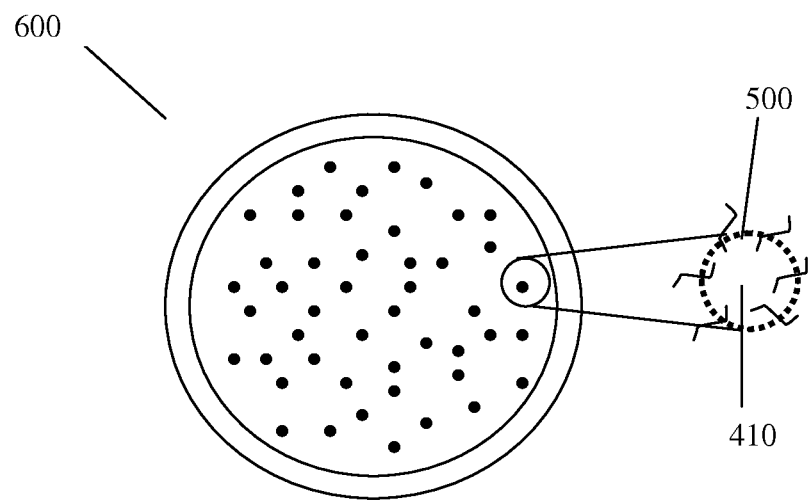
FIG. 6 is a side view of an encapsulated nucleotide tag complex with marker elements incorporated into the nanoparticles in accordance with an embodiment.
Figure 7:
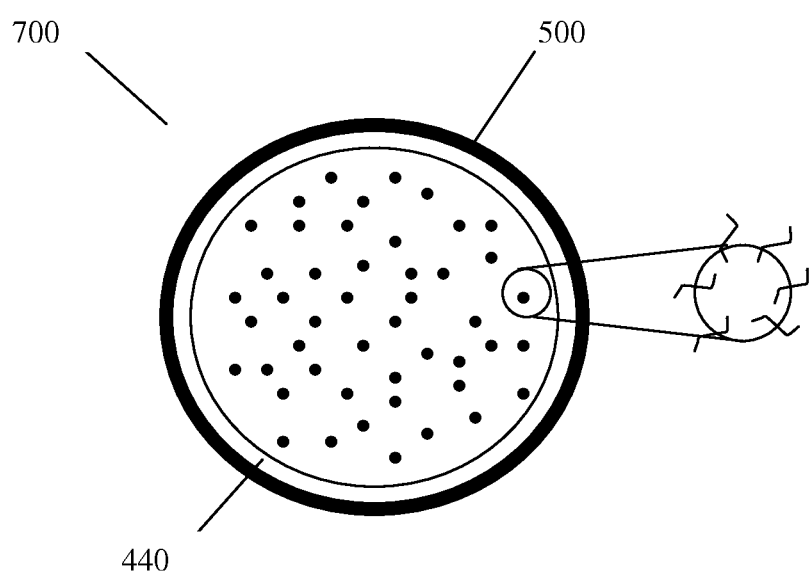
FIG. 7 is a side view of an encapsulated nucleotide tag complex with marker elements coating the outer surface of the encapsulant in accordance with an embodiment.
Figure 8:
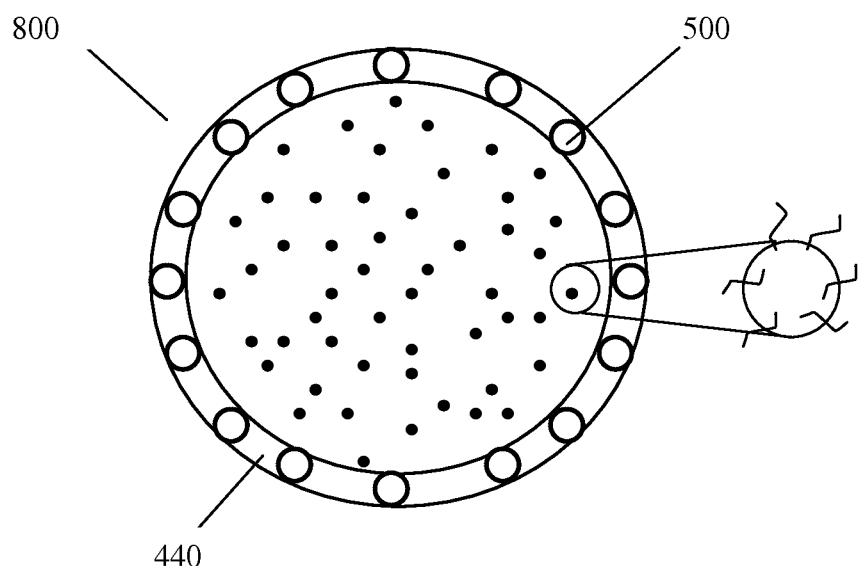
FIG. 8 is side view of an encapsulated nucleotide tag complex with marker elements coating the outer surface of the encapsulant in accordance with an embodiment.
Figure 9:
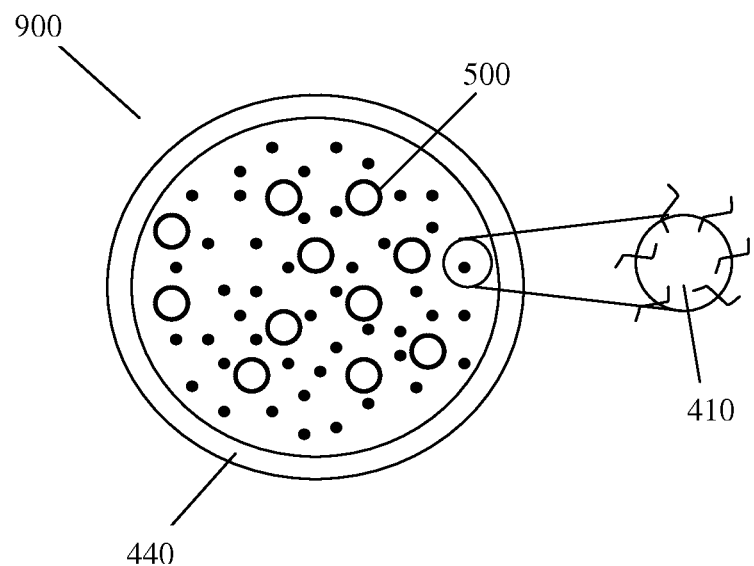
FIG. 9 is a side view of an encapsulated nucleotide tag complex with marker elements trapped inside the tag by the encapsulant layer in accordance with an embodiment.

Additional element 500 can be incorporated into the tag in a number of different ways. For example, in FIG. 5 additional element 500 is incorporated into encapsulant 440 around tag 510. In FIG. 6, additional element 500 forms a portion of the structure or base 410 that the nucleic acid is bound to. In FIG. 7, additional element 500 forms a layer on the exterior surface of encapsulant 440. In FIG. 8, additional element 500 is incorporated into the exterior layer of tag 440. In FIG. 9, additional element 500 is separate from nucleotide-support platform 410 and encapsulant 440 but is trapped within the interior of tag 900.

While the embodiments depicted in FIGS. 5-8 are shown with nucleic acid derivatizing a nanoparticle, the nucleic acid may be unencumbered, or may be attached or in communication with another form of structure or base. None of these embodiments are meant to limit the potential scope of the invention, or fully describe the possible combinations of nucleic acid, support platform, and additional elements.

At step 230 of the exemplary method depicted in FIG. 2, an item or object of interest is seeded with the prepared or packaged nucleic acid. In a preferred embodiment, the nucleic acid is placed inside or on or in the interior of the container, item, or object of interest. The nucleic acid could simply be placed there prior to the item being sealed or closed, or a more complicated form of inserting, planting, or seeding the nucleic acid could be used. The nucleic acid can be placed or seeded by hand, or can be placed or seeded using mechanics or an automated process, or a combination of methods can be used.

Indeed, novel ways release nucleic acid into a container, item, or object of interest would be beneficial. According to one embodiment, the nucleic acid is disseminated into an object or item of interest using a microcontroller connected to a light sensor and an electronic match. The nucleic acid would be sealed into a small vessel that contains a minute amount of explosives. The microcontroller would be programmed to ignite the match when the light sensor indicates that the container is closed. The microcontroller would have an integrated timing circuit to prevent accidental tag release. When the match ignites, the explosives would react, forcing the nucleic acid out of the containment vessel and into the sealed container. Many other methods of introducing nucleic acid into a container, item, or object of interest can be used.

As another example of seeding an object of interest with the prepared or packaged nucleic acid, the nucleic acid can be associated with or incorporated into security components such as a security seal, tape, ink, or glue. For example, the nucleic acid tag can be placed between two layers of a security seal. When the seal is broken, the nucleic acid tag is released from between the layers of the seal, thereby indicating tampering. As another example, the nucleic acid tag can be associated with or incorporated into tape used to seal or shut an item of interest. When the tape is removed or altered, the nucleic acid tag is released, thereby indicating tampering. This system could be especially beneficial if the tampering individual is unaware of the nucleic acid tag's presence but attempts to replace the security seal, tape, or glue after tampering. Although the tampering may not be visually evident, it will be detected due to the release of the nucleic acid tag from the seal, tape, or glue.

At step 240 of the method, the exterior of the container, item, or object of interest is examined for the presence of the nucleic acid after the item has been closed or sealed. This optional step confirms that the nucleic acid used for tamper detection was not inadvertently placed, or did not otherwise find its way, onto the exterior of the container, item, or object of interest. Nucleic acid located on the exterior of the container, item, or object of interest prior to deployment, storage, or use of the item will result in false positives when the object undergoes downstream analysis. For example, if the object is tampered with after it is seeded with nucleic acid tag, the tag will leave the interior of the object and localize outside the interior. However, if the tag is already located outside the interior, then it will appear as if the object has been tampered with even if there has been no tampering.

If the seeded nucleic acid contains, comprises, or was distributed in connection with retroreflectors, electromagnetic waves can be used to detect the presence of seeded nucleic acid. Scanning equipment shines light on the object of interest and looks for a wave front that is reflected along a vector that is parallel to but opposite in direction from the wave's source. This suggests that retroreflective tags are present on the exterior of the object and alerts the authorities that further investigation is necessary. This rapid and cost-effective identification of retroreflective tags is especially useful for high-throughput locations such as checkpoints and border crossings. Once the retroreflective tags are detected, they can be removed from the surfaces of the object for analysis of the attached nucleic acids to identify geographic locations.

The nucleic acid can also contain, comprise, or be seeded in connection with luminescent compounds that reveal their presence from a distance. Although the preferred embodiment uses fluorescent or phosphorescent photoluminescence, other embodiments may include chemiluminesent, radioluminescent, or thermoluminescent compounds. The photoluminescent compound is chosen such that absorption of a photon with a certain wavelength by the compound causes the emission of a photon with a different wavelength. The difference between the wavelength of the absorbed photon and the wavelength of the emitted photon depends on the inherent physical properties of the chosen compound.

In the preferred embodiment, the luminescent compound absorbs and emits photons in the ultraviolet band—between 400 and 10 nanometers—of the electromagnetic spectrum. The compound is chosen to avoid interference by UV radiation from the sun. The Earth's atmosphere absorbs as much as 99% of the UV radiation emitted by the sun in the 150-320 nm range. Thus the most advantageous luminescent compound absorbs and emits photons with wavelengths below 320 nm.

As an alternative to luminescent compounds that absorb and emit photons in the 150-320 nm range, compounds that absorb and emit photons of wavelengths greater than 320 nm can be used under certain circumstances. For example, these compounds could be used during nighttime conditions or in an enclosed UV-blocking environment such as a windowless structure.

The luminescent compound can be incorporated into the nucleic acid or the support platform in a number of different ways. For example, the compound can be entirely separate from the nucleic acid or the support platform. The compound can form a layer on the exterior surface of the nucleic acid or the support platform. The compound could also coat the interior surface of the encapsulant, or be incorporated into the encapsulant. In several of the described embodiments, the encapsulant layer must be designed to prevent inhibition of excitation and emission wavelengths.

If the seeded nucleic acid or support platform contains a photoluminescent compound, electromagnetic waves can be used to detect the presence of the tags at a distance. Scanning equipment shines photons of the excitatory wavelength on the object of interest and looks for photons emitted at the proper wavelength as determined by the compound used in the tags. Detection of photons with the correct wavelength suggests that a nucleic acid-labeled tag is present and alerts the scanner that further investigation is necessary. The advantage of this system is that the scanning equipment and tag can be designed such that the individual doing the scanning does not have to be in close proximity to the object of interest.

The detection process can be automated. An individual or object of interest can be forced to travel through a scanning point containing excitation equipment and emission detection equipment. As the individual or object of interest travels through the scanning point, the equipment scans for emitted photons of a certain wavelength. When the emitted photons are detected, a computer at the scanning point automatically alerts a remotely-located entity that subsequent analysis is necessary.

In yet another embodiment of the current invention, the detected nucleic acids taken from the exterior of an object are analyzed using any method that determines the exact order of nucleotide bases. There are currently a number of different commonly-used sequencing techniques including but not limited to dye-terminator sequencing, parallel sequencing, and sequencing by ligation. Sequencing machines allow automated sequencing and can be run 24 hours a day. If PCR techniques are used, the appropriate primers are chosen based upon the types of nucleic acid and/or tags known to be in the location of interest. Prior to sequencing or amplification, it is necessary to dissolve or otherwise remove an encapsulant layer from the tag in a manner that avoids inhibition of the downstream sequencing or PCR reactions, if such a layer is present or suspected to be present. In the preferred embodiment, the encapsulant and/or agglomerate is disrupted by bead beater, a form of mechanical disruption. This one-step method avoids chemicals or extractions which could affect or inhibit PCR reactions.

In addition to the traditional sequencing techniques described above, real-time PCR and sequencing by hybridization techniques allow rapid detection of target nucleic acids. According to the real-time PCR technique, the extracted nucleic acid is placed into a well or tube that has been pre-loaded with all reagents necessary for a PCR reaction as well as a sequence-specific, nucleotide-based, fluorescently-labeled probe. As the extracted nucleic acid is amplified, the polymerase degrades the probe and releases the fluorescent reporter. The reporter immediately fluoresces and alerts the system to the presence of a nucleotide. Under the sequencing by hybridization technique, the extracted nucleic acid is labeled with a fluorescent marker and is hybridized to a DNA microarray that contains the complementary nucleotide sequence from known seeded nucleic acid. If the extracted nucleic acid hybridizes to any of the complementary nucleic acid, the fluorescent signal alerts the system to the presence of a target nucleic acid. Since both methods of analysis avoid additional analysis and require relatively inexpensive analytical equipment, they promote faster and more affordable generation of data.

There are many other methods of detection of the nucleic acid and/or nucleic acid tag. For example, the nucleic acid can be detected using any molecular technique known to be suitable or adaptable for nucleic acid quantification or qualification, including but not limited to qPCR, high resolution melt ("HRM"), mass spectrometry, direct sequencing, strand displacement, and microarrays, among many others.

At step 250 of the exemplary method depicted in FIG. 2, the container, item, or object of interest is allowed to be used for the purpose for which the tag was designed. In other words, the object can be exposed to situations where tampering is possible. For example, the object can be shipped, deployed, moved, stored, or otherwise used, among many other options. During any of these steps or uses, the object of interest can be exposed to situations where it may be illicitly tampered with. In addition to detecting illicit access to an object, the seeded nucleic acid can be used to detect breakage, leakage, damage, severe movement, or many other types of motion or activity that an object of interest may be exposed to during routine or specialized functioning.

At step 260 of the exemplary method depicted in FIG. 2, the container, item, or object of interest is examined for the presence of seeded nucleic acid. Once an object of interest is identified, the object can be examined for seeded nucleic acid using any mechanism designed to pick up nucleic acid from the surfaces of the object. For example, the exterior of the object of interest can be swabbed for nucleic acid and/or tags. If the object of interest is a person, the individual's clothes, shoes, hair, or skin can be swabbed for tags. If the object of interest is a post-blast fragment of an explosive device, the surfaces of the fragment can be swabbed for any tags that survived the explosion.

To characterize identified nucleic acid, the sequences obtained from the identified nucleic acid are compared to a database of sequences attached to seeded nucleic acid. To efficiently determine the point of origin or recent travel history of an object, individuals analyzing nucleic acid detected in the field will need access or information about the nucleic acid dispersed by the seeders. A database of seeded nucleic acid will require maximum security measures to avoid improper access and manipulation, including access protection measures such as passwords. Standard computer algorithms are used to find exact or approximate matches between a sequence in the field and a tag sequence in the database. Once such a match is found, the user can reasonably suspect that the object of interest has recently traveled through the location seeded by that nucleic acid. If the real-time PCR or sequencing by hybridization techniques are used, the identification of the seeded nucleic acid is quickly determined by equipment that scans the plate or microarray for fluorescent label.

Figure 10:
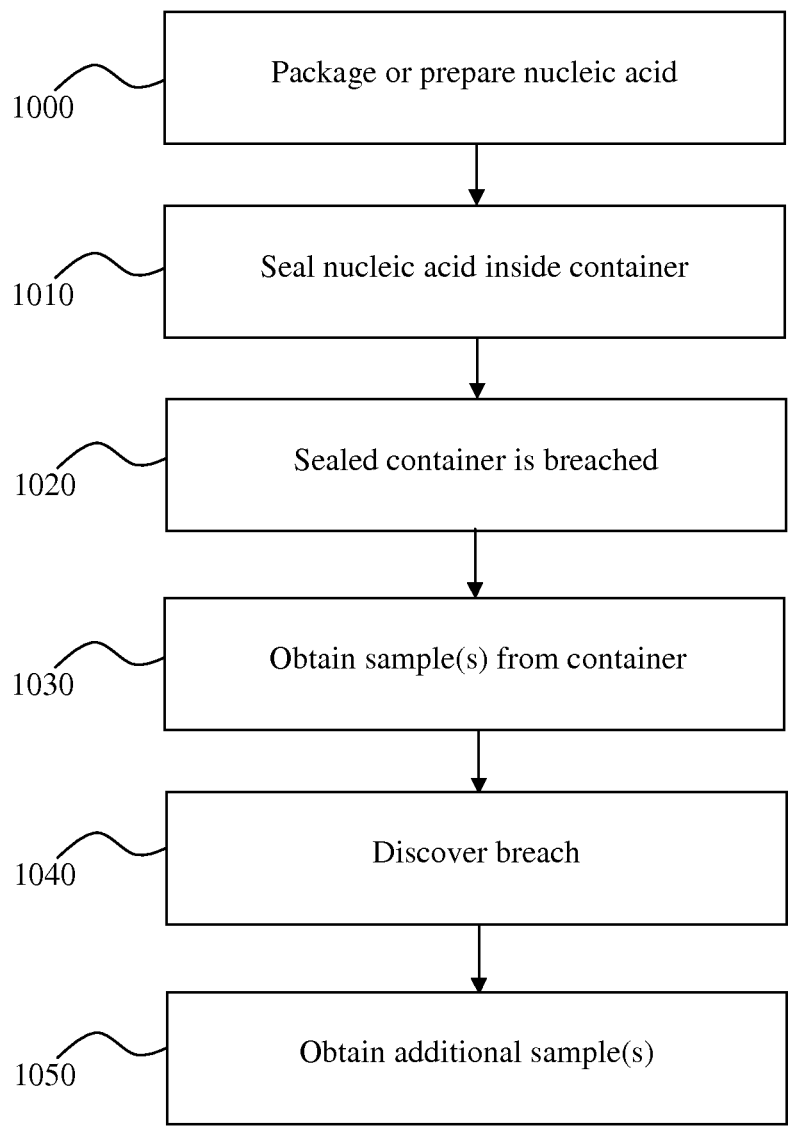
FIG. 10 is a flowchart of an exemplary process for using nucleic acid to detect tampering in accordance with an embodiment.

The flowchart in FIG. 10 summarizes a method of detecting tampering in accordance with one embodiment. At step 1000, the nucleic acid is packaged, prepared, or otherwise modified using any of a wide variety of methods, including but not limited to the methods described above. At step 1010, the prepared nucleic acid is sealed inside the item or object of interest. In a preferred embodiment, the nucleic acid is placed inside or on or in the interior of the container, item, or object of interest. The nucleic acid could simply be placed there prior to the item being sealed or closed, or a more complicated form of inserting, planting, or seeding the nucleic acid could be used. The nucleic acid can be placed or seeded by hand, or can be placed or seeded using mechanics or an automated process, or a combination of methods can be used.

As an optional step, the exterior of the container can be sampled immediately or soon after the nucleic acid is sealed inside. This optional step confirms that the nucleic acid used for tamper detection was not inadvertently placed, or did not otherwise find its way, onto the exterior of the container, item, or object of interest. Nucleic acid located on the exterior of the container, item, or object of interest prior to deployment, storage, or use of the item will result in false positives when the object undergoes downstream analysis.

At step 1020 of the method, the sealed item of interest is breached, altered, tampered with, or otherwise modified in such a way as to release some of the nucleic acid sealed inside the item of interest. For example, if the item of interest is a container of goods, the nucleic acid sealed inside the container could be released if the container is opened or damaged. As just one example, medical goods such as pharmaceuticals are often shipped or distributed long distances, exposing them to potential tampering. It is vital, however, that the pharmaceuticals are not modified, altered, or tampered with during shipping or distribution. Accordingly, the packaging containing pharmaceuticals can be sealed with the prepared nucleic acid inside. If the packaging is tampered with, nucleic acid will be released and tampering can be detected.

At step 1030 of the method, one or more samples are obtained from the exterior of the item of interest in order to determine whether the sealed nucleic acid has been released, and thus whether there has been tampering. The sample can be analyzed using any method capable of: (i) detecting nucleic acid or the platform; and, optionally, (ii) determining the order of the nucleotide bases in the nucleic acid (in order to obtain any information stored within). PCR amplification and SNP genotyping are just two examples of methods that can detect the nucleic acid and determine a sequence of or within that nucleic acid.

At step 1040 of the method, analysis of the sample(s) taken from the item of interest reveals that there is nucleic acid present, and thus that the item has been damaged, tampered with, or otherwise modified. Further investigation will be required to determine when or how the item was modified, and who performed the modification. For example, at optional step 1050 of the method depicted in FIG. 2, further samples can be obtained in order to examine questions related to the tampering. Handlers may be sampled to determine if they have been labeled with the nucleic acid. Other surfaces, including locations through which the item traveled, can also be sampled to analyze the tampering. If the item traveled through multiple locations such as a truck, a warehouse, and a distribution center, each of these locations can be sampled to, for example, learn more about when and where the tampering occurred, and to create an approximate timeline of the item and the tampering.

Figure 11:
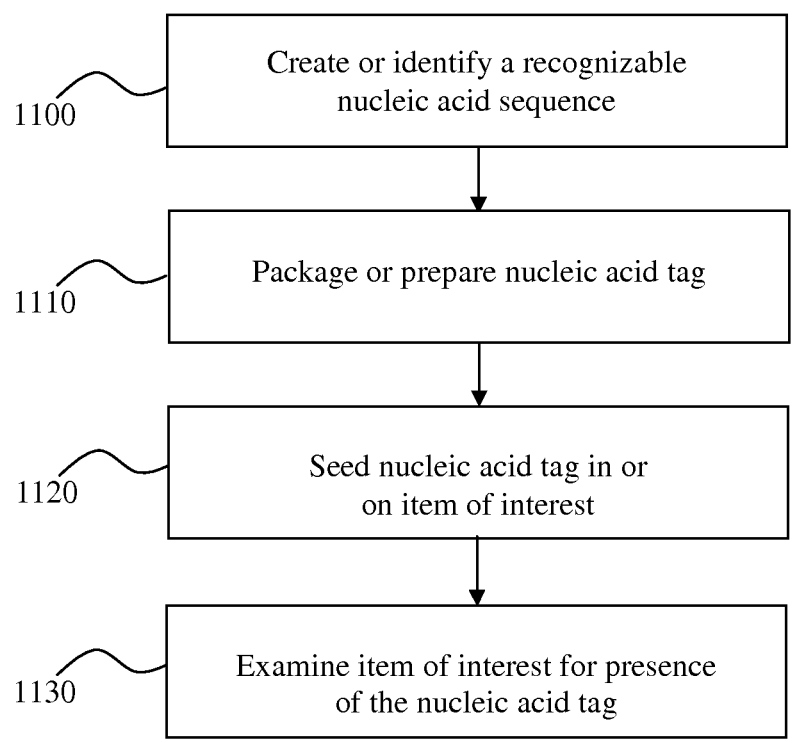
FIG. 11 is a flowchart of an exemplary process for using nucleic acid for authentication in accordance with an embodiment

In addition to directly detecting tampering, the nucleic acid tags described herein can be used for authenticating an object or thing. FIG. 11 is a schematic representation of an embodiment of an authentication method according to one aspect of the invention. More specifically, the figure represents a method for authenticating an object that has been labeled with a seeded nucleic acid tag. The item can be, for example, any person or object of interest.

As an initial step 1100 of the method, a suitable nucleic acid sequence is characterized or created according to any of the methods described herein. In one embodiment, the sequence ranges from a short oligonucleotide to an entire genome and is generated through any of the various known methods of natural or artificial nucleic acid synthesis. The nucleic acid can be completely composed of either natural nucleic acids which normally compose the genomes of organisms, artificial nucleic acids, or any combination thereof. In another embodiment, the nucleic acid molecules contain primer-binding sequences surrounding unique nucleotide sequences. The unique nucleotide sequence contained between the primers can encode information that corresponds to an identification, location, date, time, or other data specific to that unique sequence. Since analysis of every nucleic acid molecule can use the same primers, the analysis can be performed faster and more efficiently.

The nucleic acid tag can be used not only for simple binary (i.e., "yes/no") authentication, but also for informational authentication. In the example of a pharmaceutical label, the nucleic acid tag can not only verify that the item is authentic, it can further comprise information about the pharmaceutical's components, date of manufacture, date of expiration, place of manufacture, lot number, and many other pieces of information. In the example of a food label, the nucleic acid tag can not only verify that the item is authentic, it can further comprise information about the food's components, the location it was grown and/or processed, date of processing, date of expiration, the lot number, and many other pieces of information.

At step 210 of the method shown in FIG. 11, the nucleic acid is packaged, prepared, or otherwise modified prior to use. Preparation of the nucleic acid can range from little or no preparation or modification to an extensive series of steps for modifying the nucleic acid. For example, the nucleic acid can be used to derivatize nanoparticles, as described herein, or can be added to another structure or base. As another example, the nucleic acid can be packaged into an appropriate tag complex as described elsewhere in this specification.

At step 1120 of the method depicted in FIG. 11, an item or object of interest to be authenticated is seeded with the prepared or packaged nucleic acid. The nucleic acid tag can be placed inside or on or in the interior of the container, item, or object of interest. The nucleic acid could simply be placed there prior to the item being sealed or closed, or a more complicated form of inserting, planting, or seeding the nucleic acid could be used. The nucleic acid can be placed or seeded by hand, or can be placed or seeded using mechanics or an automated process, or a combination of methods can be used. For example, the nucleic acid tag can be associated with or incorporated into security components such as a security seal, tape, ink, or glue. The nucleic acid tag can be placed between two layers of a security seal, or can be associated with or incorporated into tape used to seal or shut an item of interest.

As yet another example, the nucleic acid tag can be seeded or placed in or on or otherwise associated with a sensitive product. The nucleic acid tag can be associated with or otherwise seeded in or on a label of a pharmaceutical, food, medicine, or other commercially or security sensitive object.

As another example, the tag can be incorporated into the material comprising all or a portion of the actual item or object of interest. For example, the tag can be seeded into credit cards, or another plastic or polymer structure, by seeding the tag directly into a precursor component such as the PVC, PVC-Co-A, or other polymer precursor before the credit card is formed. Given the ubiquitous nature of plastic and complex polymers in all aspects of manufacturing, distribution, and storage, for example, there are an almost unlimited number of possible applications for this seeding technique.

Once the item of interest to be authenticated is labeled or otherwise seeded with the nucleic acid tag, the container, item, or object of interest is allowed to be used for the purpose for which the tag was designed. In other words, the object can be exposed to situations where authentication may be necessary. For example, the object can be shipped, deployed, moved, stored, or otherwise used, among many other options. During any of these steps or uses, the object of interest can be exposed to situations where it may be illicitly tampered with. In addition to detecting illicit access or other tampering or alteration of an object, the seeded nucleic acid can be used to detect breakage, leakage, damage, severe movement, or many other types of motion or activity that an object of interest may be exposed to during routine or specialized functioning.

At step 1130 of the method depicted in FIG. 11, the authenticity of the container, item, or object of interest can be confirmed by determining the presence of seeded nucleic acid using any of the methods described herein. For example, once an object of interest is identified, the object can be examined for seeded nucleic acid using any mechanism designed to pick up nucleic acid from the surfaces of the object. For example, the exterior of the object of interest can be swabbed for nucleic acid and/or tags. The nucleic acid can be identified and characterized using any of the methods, systems, devices, or molecular techniques described or mentioned herein.

As another example of a nucleic acid tag detection system, the tag can be detected using any of a number of electrochemical detection systems, including but not limited to luminescence, surface plasmon resonance, cyclic voltammetry, electrochemical impedance spectroscopy, or quartz crystal microbalance. The step of detecting the presence of the nucleic acid tag in the sample may also comprise atomic force microscopy.

Figure 12:
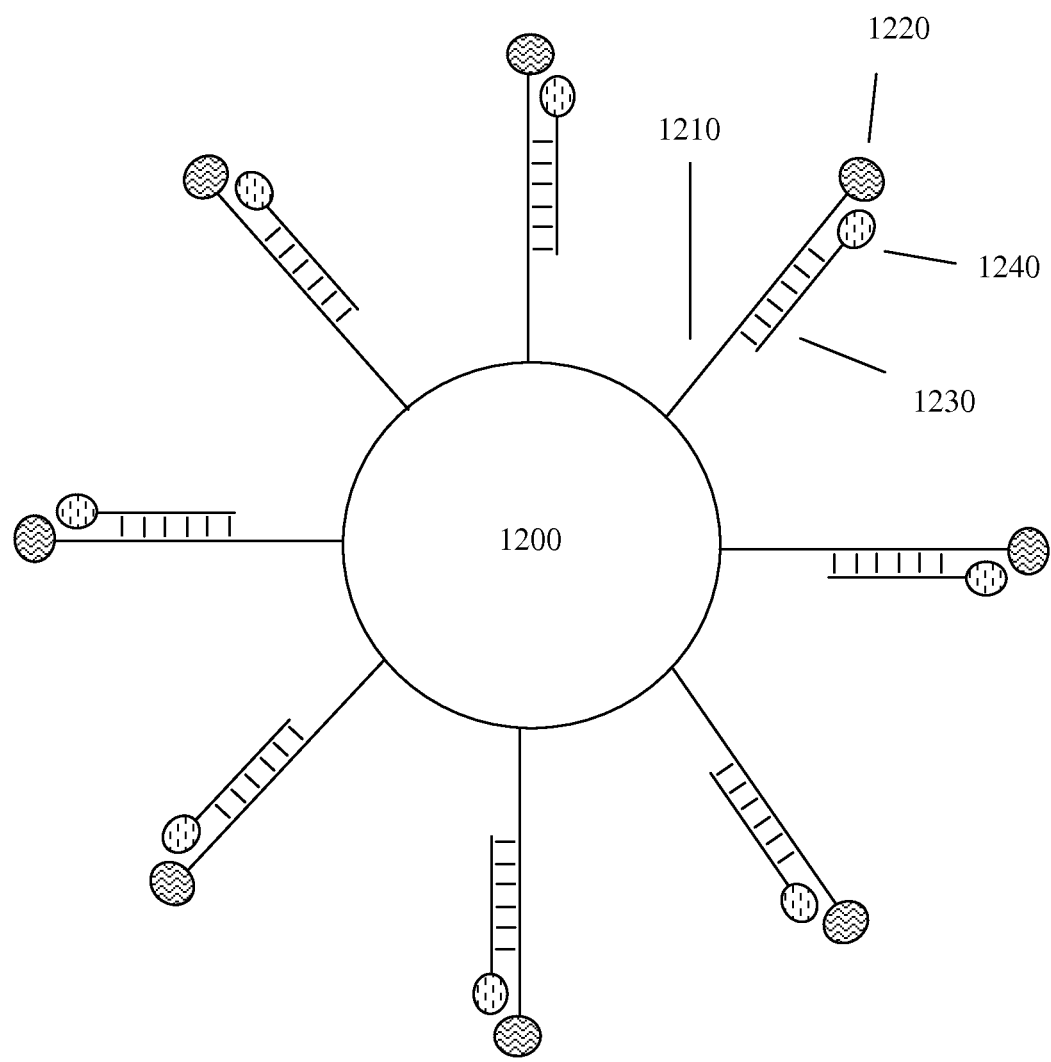
FIG. 12 is a nucleic acid tag detection system in accordance with an embodiment.
Figure 13:
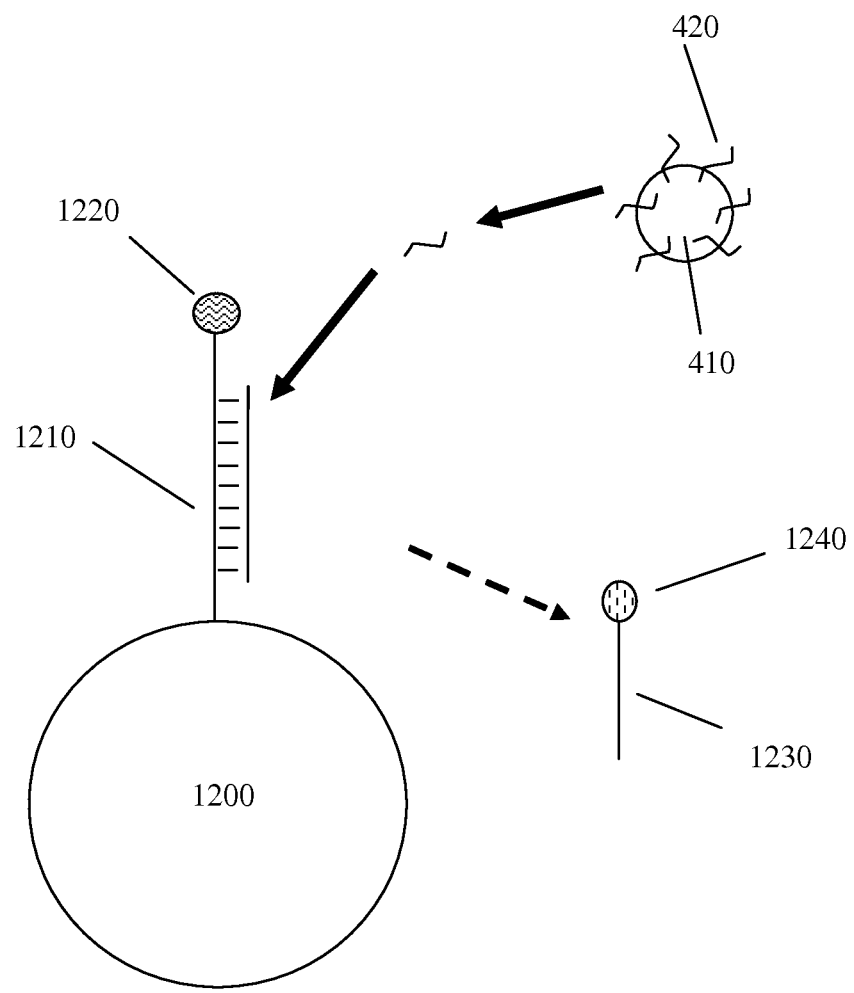
FIG. 13 is a nucleic acid tag detection system in accordance with an embodiment.

As another example of a nucleic acid tag detection system, a strand displacement method or kit can be used to detect and characterize the nucleic acid tag. An example of this detection system is depicted in FIGS. 12 and 13, although numerous variations are possible. A functionalized authentication bead 1200 comprises one, several, or many different authentication reporters. An authentication reporter can comprise a master segment 1210 and a reporter segment 1230, where the segments are comprised of, for example, a nucleic acid or other compound capable of reversible interaction. In this example at least a portion of the nucleic acid of reporter segment 1230 is complementary to at least a portion of the nucleic acid of master segment 1210, and the two segments directly interact in the absence of a target segment. In one application, reporter segment 1230 is functionalized with a fluorophore 1240 and master segment 1210 is functionalized with a quencher or other component 1220 that decreases the fluorescence intensity of fluorophore 1240. In the example shown in FIG. 12, for example, each reporter segment can comprise a different fluorophore.

It should be noted that fluorophore 1240 can comprise other methods of reporting, including but not limited to metal- or chemiluminescence-labeling.

Probe-target hybridization is usually detected and quantified by detection of fluorophore-, silver-, or chemiluminescence-labeled targets to determine relative abundance of nucleic acid sequences in the target.

To detect the presence of a target nucleic acid tag, the unique nucleic acid sequence 420 from nucleic acid tag 410 is added to the system. The tag could be obtained from a target or person of interest, for example. The tag can optionally be processed in some manner in order to amplify and/or release the DNA from the nucleic acid tag for identification by the system depicted in FIGS. 12 and 13. As shown in FIG. 13, at least a portion of nucleic acid 410 of tag 420 is complementary two at least a portion of master segment 1210 such that when nucleic acid 410 is added to the system, it binds master segment 1210 and displaces reporter segment 1230. Toehold strand displacement is just one example of a strand displacement approach that could be utilized in this system to promote the displacement of reporter segment 1230 by target sequence 410. As a result of the displacement of reporter segment 1230, fluorophore 1240 is no longer influenced by quencher 1220 and can fluoresce with proper excitation.

Figure 14:
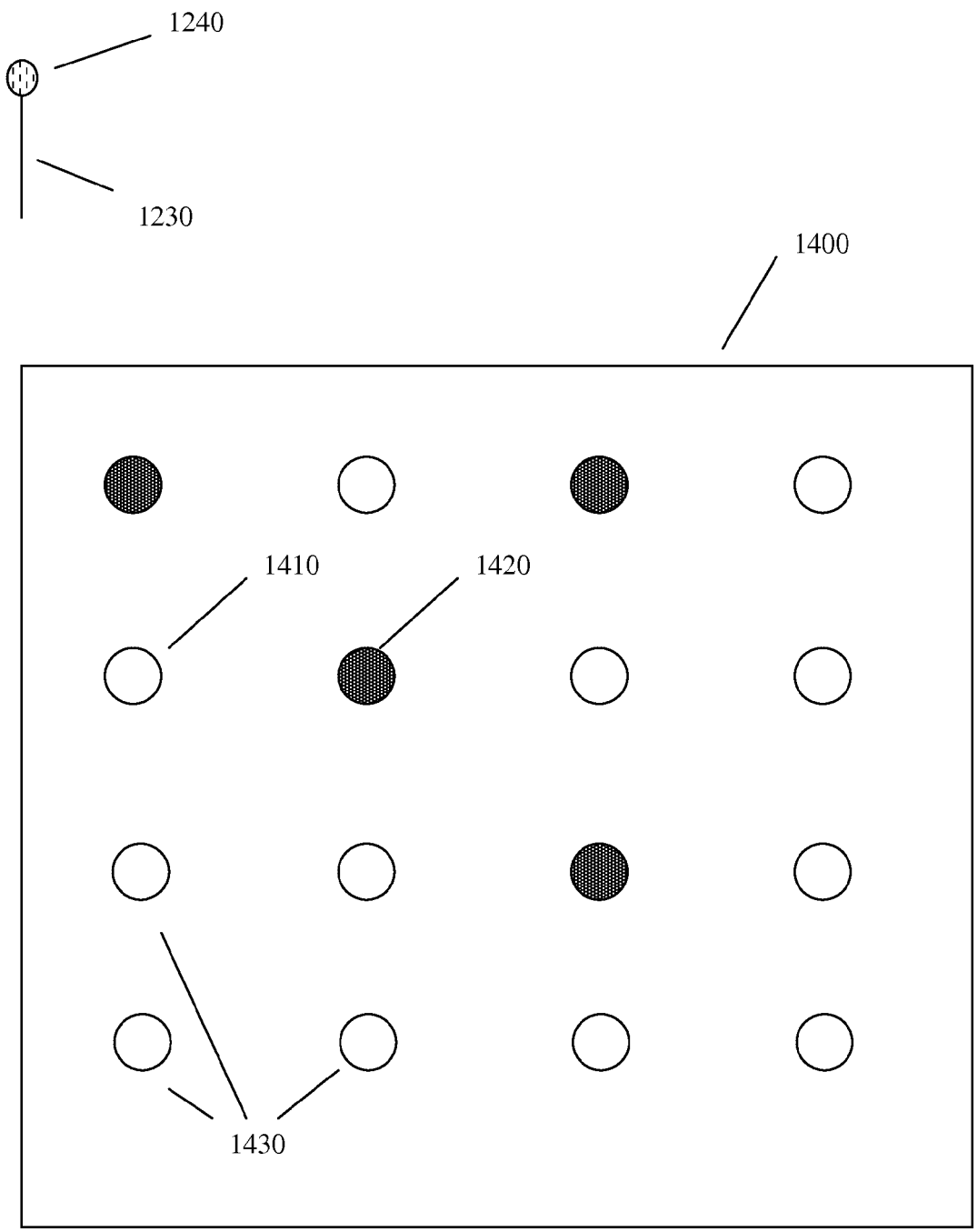
FIG. 14 is a nucleic acid tag detection system in accordance with an embodiment.

To refine detection, liberated reporter segment can also be washed, for example, away from functionalized authentication bead 1200 and added to an advanced detection system. For example, the advanced detection system 1400 depicted in FIG. 14 comprises a 4×4 grid of nucleic acid sequence spots 1430, at least a known portion of which are complementary to reporter segment 1230 (although the grid can comprises thousands, millions, or more complementary sequences). Liberated reporter segment 1230 is allowed to bind to the one or more complementary nucleic acid sequence spots 1430, thereby creating a reporter pattern of positive hits 1420 (where the nucleic acid sequence spot is complementary to reporter segment 1230) and negative hits 1410 (where the nucleic acid sequence spot is not complementary to reporter segment 1230). For example, a specific pattern has been created in FIG. 14 which can provide identifying and/or characterizing information about the sample that has been obtained and processed; not only are tags present, but their specific sequence can characterized based on the binding pattern. Complicated mixtures of two or more different nucleic acid tags 420 can be identified in this manner as well as long as different patterns are created (or different fluorophores are used).

The pattern can be detected using a variety of detection tools. For example, a microarray scanner or other device comprising the necessary excitation source and optics can be used to excite the labeled detection system 1400. In one application, a smart phone or other wireless or wired handheld device can be used to detect the binding pattern and subsequently identify and/or characterize the tag(s) in the sample. In this application, the user creates or receives the labeled detection system 1400 using one or more of the methods described herein, and then uses the handheld device to identify and/or characterize the bound tag(s). For example, to create a defined wavelength—and preferably a narrowed wavelength—such that one or more of the possible fluorophores are excited, the user can place a specific colored sticker or filter over the flash or other light source of the handheld device. Activating the flash or other light source will cause light to be filtered by the colored sticker or filter such that substantially only the defined wavelength reaches labeled detection system 1400. The camera or other optical input of the handheld device can then capture an image of the activated and fluorescing pattern on the detection system, and in one application a filter can be placed over the optical input to clarify or otherwise process the incoming image for improved detection. According to one embodiment, the handheld device can then query a database—either stored locally on the handheld device or stored remotely (including, for example, queries sent over the Internet or another wired or wireless network)—to identify and/or characterize the identified pattern. Optionally, the handheld device can convert or reduce the digital image and pattern to a pre-determined code or other simplified query to reduce the size of the query or to maintain security during transmission over wired or wireless networks. Information about the identified and/or characterized tags can then optionally be returned to the user or otherwise processed for cataloging or further analysis. According to one embodiment, the user can then apply a new colored sticker or filter in order to query other possible fluorophores. These applications have particularly beneficial applications in the field.

Although the present invention has been described in connection with a preferred embodiment, it should be understood that modifications, alterations, and additions can be made to the invention without departing from the scope of the invention as defined by the claims.

What is claimed is:

1. A method for detecting tampering, the method comprising:
    sealing within an item of interest a nucleic acid tag comprised of a nanoparticle nucleotide-support platform attached to a nucleic acid molecule, wherein the nucleic acid tag is sealed within the item of interest such that the tag cannot be detected unless a third-party tampers with the item of interest; and
    examining an exterior surface of the item of interest for the presence of the nucleic acid tag, wherein the presence of the tag on the exterior surface indicates tampering.

2. The method of claim 1, wherein the step of sealing the nucleic acid tag within the item of interest comprises releasing the nucleic acid tag inside the item of interest after the item of interest has been sealed.

3. The method of claim 1, wherein the nucleic acid molecule is composed of nucleotides selected from the group consisting of ribonucleotides, deoxyribonucleotides, and nucleotide analogues.

4. The method according to claim 1, wherein the nucleic acid molecule is an oligonucleotide.

5. The method according to claim 1, wherein information about the item of interest is contained within the nucleic acid molecule.

6. The method according to claim 1, wherein the nucleic acid tag includes an encapsulant.

7. The method of claim 1, wherein the step of sealing the nucleic acid tag within an item of interest comprises incorporating the nucleic acid tag within a label, package, seal, adhesive, or polymer.

8. The method of claim 1, wherein the step of sealing the nucleic acid tag within an item of interest comprises incorporating the nucleic acid tag into a precursor of the item of interest.

9. A method for detecting tampering with an item of interest, the method comprising:
    obtaining a nucleic acid tag, wherein said nucleic acid tag comprises a nanoparticle nucleotide-support platform attached to a nucleic acid molecule, and wherein information about the item of interest is contained within the nucleic acid molecule;

sealing the nucleic acid tag within the item of interest, wherein the nucleic acid tag is released inside the item of interest after the item of interest has been sealed; and examining an exterior surface of the item of interest for the presence of the nucleic acid tag, wherein the presence of the tag on the exterior surface indicates tampering.

\* \* \* \* \*